United States Patent [19]

Locke et al.

[11] 4,005,495
[45] Feb. 1, 1977

[54] CERAMIC CAP BONE PROSTHESIS AND METHOD OF IMPLANTATION

[75] Inventors: Helmut Locke, Lauf, Pegnitz, Germany; Martin Salzer, Vienna, Austria

[73] Assignee: Rosenthal Technik AG, Germany

[22] Filed: Apr. 16, 1976

[21] Appl. No.: 677,799

[30] Foreign Application Priority Data

Aug. 9, 1975 Germany .................. 2535649

[52] U.S. Cl. .................. 3/1.91; 3/1.913; 128/92 CA
[51] Int. Cl.² .................. A61F 1/24
[58] Field of Search .................. 3/1.9–1.913; 128/92 C, 92 CA

[56] References Cited

UNITED STATES PATENTS

| 2,668,531 | 2/1954 | Habonsh | 128/92 CA |
| 3,521,302 | 7/1970 | Muller | 3/1.91 |
| 3,925,824 | 12/1975 | Freeman et al. | 3/1.912 |

FOREIGN PATENTS OR APPLICATIONS

| 1,164,019 | 2/1964 | Germany | 128/92 CA |
| 2,318,459 | 10/1974 | Germany | 3/1.912 |

Primary Examiner—Ronald L. Frinks
Attorney, Agent, or Firm—Ostrolenk, Faber, Gerb & Soffen

[57] ABSTRACT

Endoprosthesis for bone joint, or the like, in the form of a spherical cap having a frusto-conical opening into it; the end of the bone is shaped to matingly fit into the opening into the cap; a thrust plate passes through the bone into the cap opening to transfer thrust away from the end of the bone; grooves in the cap to promote adhesion to the bone.

13 Claims, 6 Drawing Figures

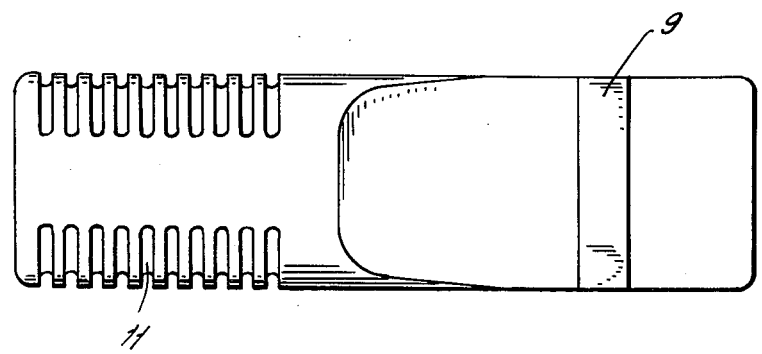
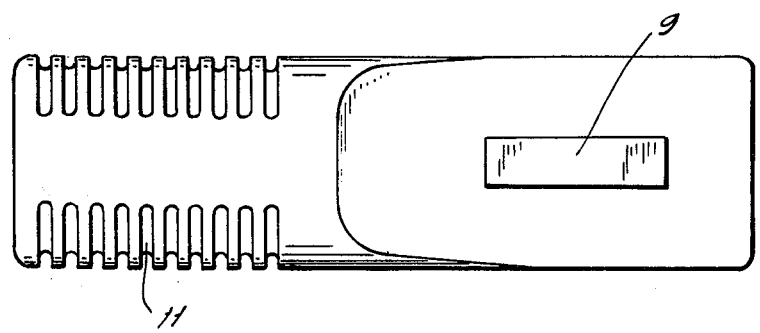

CERAMIC CAP BONE PROSTHESIS AND METHOD OF IMPLANTATION

BACKGROUND OF THE INVENTION AND DESCRIPTION OF THE PRIOR ART

The invention relates to an implant for an improved endoprosthesis, of the type shown in German Pat. No. P 24,54,181.9. The implant is compatible with the skeleton and also forms a strong connection between the prosthesis and the bone immediately after the implantation without the use of bone cement.

An artificial bone joint replacement comprised of sintered oxide ceramic material is proposed in German Auslegeschrift No. 2,318,459. This publication describes a bone joint head on a worked femur head or a joint roller which is in engagement with the artificial joint socket. The socket also is comprised of sintered high-melting point metallic oxides. This type of artificial joint has a number of difficulties in use. The femur bone head can be worked only poorly into a prismatic polygon. The great variations among femur heads does not permit too close a fit of the implant on every femur head. Moreover, there is a danger of bone fracture in the region of the neck of the femur as a result of unpredictable loading, since considerable torques occur when the implant is screwed into the bone with a self-tapping thread.

A report by F. Betzel: "Kunststoffe in der plastischen Chirurgie der Gelenke" (Plastics in plastic surgery of the joints), which appeared in "Melsunger Medizinischpharmazeutische Mitteilungen", Issue 100 (1963), pages 2478–86, notes that endoprostheses were introduced by the Judet brothers and had their first clinical applications in 1948. Endoprostheses were then made of metal and plastic. Plastic hip surgery with Pyrex-Bakelite caps by Smith-Peterson occured. Because of pain caused the wearer of the prostheses by loading or stress and by his movement, because of the occurence of infections, because of prosthesis material damage and, in some cases, also on account of a degenerative shrinkage of the head and neck stump of the bone, such plastic prosthesis caps often have had to be removed soon after implantation. Such a cap often cannot long remain on the bone stump because the cap fits on loosely.

According to German Utility Model No. 75 09 026, elimination of the above described disadvantages has been attempted by uniting the loosely mounted prosthesis cap closely to the joint head, using as little bone cement as possible. Such a cap is made from metal and it is uneven on its inside surface to engage the bone and the cement. The cap has an opening leading to the outside for insertion of the cement.

Other cap shaped composite endoprostheses of metal and plastic are known from Swiss Pat. No. 560,538 and from German Pat. No. 876,739. The artificial joint head is spherically or mushroom shaped and the anchoring stem or shank mounted on the underside of the prosthesis may simply be straight or curved.

Although these implants permit careful treatment of the bone and also do not aggravate bleeding conditions during the implantation, they have not proven successful in practice because the metal and plastics materials employed do not promote long life for the implanted endoprosthesis. Moreover, with ceramic implants, experience has shown that the design possibilities have not yet been fully exhausted. In particular, in the use of these artificial joint replacement parts, various disadvantages, which can be traced back to the design of the hip joint prosthesis, have been manifest.

SUMMARY OF THE INVENTION

The invention provides a one-part or multi-part implant for an improved endoprosthesis. The implant complies with the structural conditions of the skeleton and also forms a strong connection with the bone immediately after the implantation without employing bone cement. Wear and corrosion resistant and toxically unobjectionable materials are used. At the same time, simplified manufacture of the implant is achieved. Moreover, with the new implant, minimal resection of the bone is required and the implantation permits decreased operative intervention. The implant includes a spherical cap for a bone which serves as part of the joint. The cap has a central bone receiving opening.

Firm seating of the implant is ensured by working or shaping of the bone to fit accurately into the implant. In a preferred arrangement, the bone is generally conically shaped or worked and the interior of the ceramic cap has a matingly shaped opening into which the bone end is placed. The mating conical shaping improves mechanical force flow and results in an optimum pressure which does not allow any bone tissue damage to occur. In contrast to other stem or shank prostheses, only a minimum stiffening of the femur will occur with this cap prosthesis. Also, loading of the implant is possible immediately after the implantation, so that the length of an implant recipient's stay in a hospital can be considerably shortened.

A thrust plate extends from the cap to the femur neck. This transfers the initiated forces from the head of the femur to the neck of the femur. In a modified form, the thrust plate includes a projection as a supplementary mechanical retaining means.

An advantageous development of the thrust plate comprises providing a longitudinally extending threaded hole in the lower part of the thrust plate for the purpose of effecting supplementary fixing to the bone by means of a screw.

The spherical cap central opening has circular or spiral grooves in it extending around the axis of the thrust plate for promoting bone engagement. In a variation, the internal cone of the central opening has axially extending recesses running generally parallel to the axis of the thrust plate. In a further variation, the inner surface of the spherical cap has an axially extending array of projections. The implant is formed from wear and corrosion-resistant materials which are also toxically unobjectionable. Preferably, an oxide ceramic, in particular highly pure aluminum oxide, is employed for the spherical cap and for the thrust plate.

The advantages of the cap shaped form of construction of the ceramic implant result from the use of biocompatible materials and through the application of cement-free implantation. Even young patients can be provided with hip joint prostheses which lasts a long time and are stable. By use of the spherical ceramic cap, implantation procedures can be kept rather minor.

Although the use of the cap prosthesis of the invention is described essentially for human beings, these improved ceramic bodies are also suitable for veterinary purposes.

A spherical cap prosthesis formed in this manner may be used as part of a complete prosthesis. But for this, an acetabulum is also necessary. The spherical cap may also be employed as a partial prosthesis. In this case, the external diameter of the ball of the prosthesis is made larger and it then engages in the natural acetabulum.

Accordingly, it is the primary object of the invention to provide an improved endoprosthesis.

It is another object of the invention to implant such a prosthesis with minimal harm.

It is a further object of the invention to firmly attach the prosthesis permanently without chance of weakening and without cement being required.

These and other objects of the invention are realized with the structures and method described below.

The invention is described in detail hereinafter with reference to a constructional form of the cap prosthesis which is shown in the drawings by way of example.

BRIEF DESCRIPTION OF THE DRAWINGS

FIGS. 5 and 6 are plan views of two embodiments of the thrust plates.

DESCRIPTION OF A PREFERRED EMBODIMENT

Figure 1:
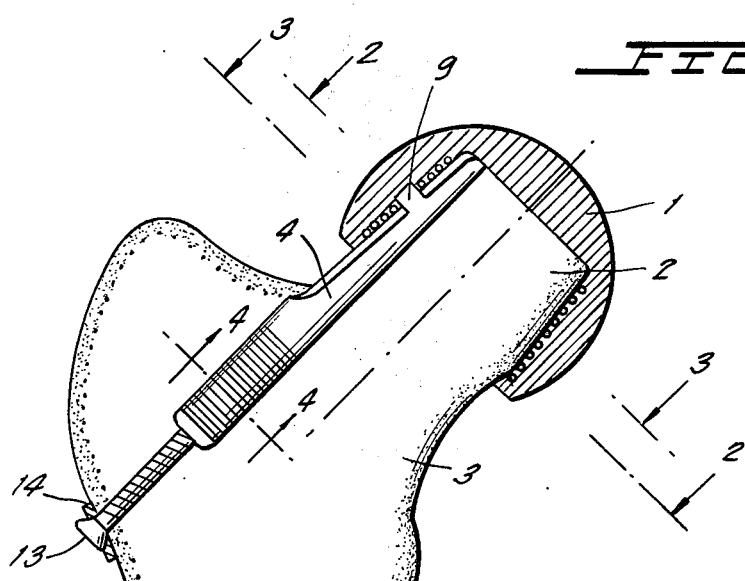
FIG. 1 is a central longitudinal section through a femur with a prosthesis mounted thereon.

As can be seen from FIG. 1, the ceramic implant according to the invention principally is comprised of a spherical cap 1 of ceramic material. In order to obtain a friction free and wear resistant implant, the spherical cap 1 is polished on its exterior surface. An optionally insertable below described thrust plate 4 may be used. At one side, the cap 1 has a large central opening which is frusto-conically shaped. The cap is secured to the worked femur 10 by means of thrust plate 4 and a draw screw 13.

Before attaching cap 1 to the damaged femur 10, the natural, generally spherically shaped femur head 2 is first altered to a cylindrical shape using a hole saw. This working or dressing of the bone is effected in a plurality of stages. The process is begun using a larger hole saw. It is determined whether the cylindrical stub of the bone is located centrally with respect to the neck of the femur and, if necessary, the central location of the cylindrical stub is established with a small hole saw. Next, the cylindrical stub is formed into a frusto-conical shape with a special tool. The cone angle is between 1:10 and 1:6. The height of the cone is determined with a suitable gauge and the projecting end is cut away. The cone of the femur is shaped to mate with the conical opening in cap 1.

In order to enhance the hold of the spherical cap 1 on the conically reshaped femur head 2, a thrust plate 4 may be inserted in the bone 10. An opening in the femur for the thrust plate 4 and also for the draw screw 13 are produced with drill and chisel. The opening for the thrust plate 4 is placed so that the thrust plate will engage the cap 1 when the latter is emplaced.

To secure the implant 1, the thrust plate 4 is first placed in its opening. Then the cap 1 is pushed over it. The cap 1 is next forced onto the conical bone stump 2 together with the thrust plate 4. The implant is now seated in closely conforming manner on the conical bone stump. By means of the thrust plate 4, cap 1 is additionally secured. A surgical screw 13 is introduced into the threaded hole 11 in thrust plate 4 and it is screwed tight. For protection of the bone, washer 14 is placed at the starting point on the bone 10.

Figure 2:
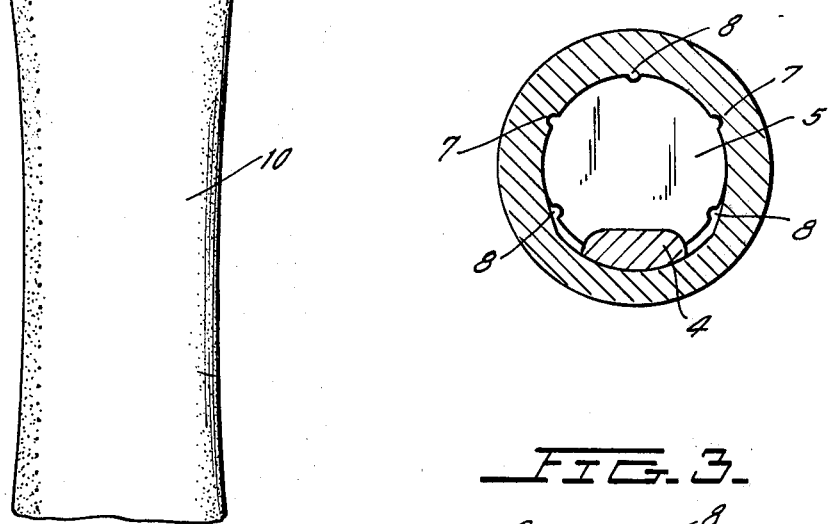
FIGS. 2 and 3 are respective cross sectional views along the lines 2—2 and 3—3 of FIG. 1.
Figure 3:
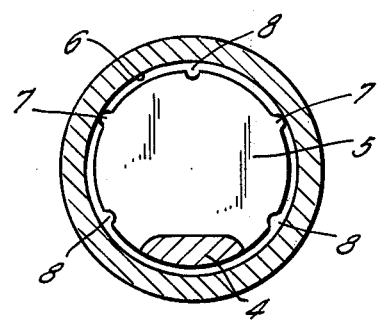

FIGS. 2 and 3 show the circular recesses 6 extending annularly around cap 1 and around thrust plate 4 and also show the transversely extending axial recesses 7 for securing the prosthesis 1 durably to the bone. Projections or ribs 8 extend axially around cap 1. The recesses 6, 7 and projections 8 promote durable anchoring of the implant to the bone by the natural bone tissue growth and the adhesion of the tissue. The projections 8 serve for the primary fixing of the implant and for securing it against rotary movement.

Figure 4:
FIG. 4 is a cross sectional view through a thrust plate and taken along the line 4—4 of FIG. 1.

In FIGS. 1 and 5, the upper or cap part of the thrust plate 4 is of generally frusto-conical form to mate with the opening in cap 1, whereas the lower part of plate 4 is more elliptically shaped in cross section (FIGS. 2–4). The grooves 11 on the exterior of thrust plate 4 are also intended to produce durable anchoring of the implant part by invasion or ingrowth of bone substance, as in the case of the recesses 6 and 7. Projecting above the surface of plate 4 is the projection 9 that is so placed and directed that the back surface of the thrust plate 4 is applied in closely conforming manner against the circular thrust plate receiving profile of the bone stump 2 while projection 9 engages in a corresponding recess in the spherical cap 1. Projection 9 prevents the cap 1 being pulled off the worked femur head 2. The projection 9 may be oriented at either of two mutually perpendicular orientations (FIGS. 5 and 6). This makes no difference to its functioning.

Although the present invention has been described in connection with a preferred embodiment thereof, many variations and modifications will now become apparent to those skilled in the art. It is preferred, therefore, that the present invention be limited not by the specific disclosure herein, but only by the appended claims.

We claim:

1. Improved implant for an endoprosthesis comprising;
   a cap to be placed over the end of a bone; said cap being generally spherical in shape on its exterior; said cap having an opening into one side thereof and extending into its interior; said opening being defined by side walls shaped to form said opening into a shape that securely seats and fits on the end of the bone;
   a thrust plate extending into said opening and having engagement means engageable with said side walls and being in engagement therewith; said thrust plate extending a distance away from said cap to an end of said thrust plate; fastening means in engagement with said thrust plate end for holding said thrust plate to the bone.

2. The implant of claim 1, wherein said cap opening side walls are generally conically tapered narrower moving inwardly into said opening.

3. The implant of claim 2, wherein said thrust plate has a cap portion that extends into and engages said cap opening side wall; said thrust plate cap portion being conically tapered along its length to mate with and engage said side walls.

4. The implant of claim 2, wherein said opening side walls have grooves into them to more securely engage the bone.

5. The implant of claim 4, wherein said grooves are intersecting.

6. The implant of claim 4, further comprising projecting ribs on said side walls and extending axially through said opening.

7. The implant of claim 1, wherein said thrust plate engagement means comprises a projection above a surface of said thrust plate and in engagement with said opening side walls.

8. The implant of claim 1, wherein said fastening means comprises a screw and a mating opening into said thrust plate end into which said screw is tightened for drawing said cap against the bone.

9. The implant of claim 1, wherein said spherical cap and said thrust plate are comprised of an oxide in the form of a ceramic material.

10. The implant of claim 9, wherein said ceramic material is aluminum oxide.

11. Process for attaching an endoprosthesis on a bone, comprising the steps of: providing a cap having a spherical exterior and an opening into it which is generally conical in shape;

shaping the end of a bone to be generally conical in shape and to mate with the walls of the opening in the cap;

forming a bone opening through the bone from below the end top to the cap;

passing a thrust plate through the bone opening and into the cap opening thereby to transfer the forces on the cap along the thrust plate to the area of the bone below the end.

12. The process for attaching an endoprosthesis of claim 11, wherein the bone opening extends through the bone and passes out of the bone at both ends thereof;

fastening the thrust plate to the bone at the end of the thrust plate away from the cap.

13. The implant of claim 12, comprising the further steps of: forming the cap with a spherical exterior shape;

forming a conically shaped opening into the cap.

* * * * *